United States Patent [19]
Sunkel et al.

[11] Patent Number: 5,691,361
[45] Date of Patent: Nov. 25, 1997

[54] 1,4-DIHYDROPYRIDINE DERIVATIVES, A PROCESS FOR THEIR PREPARATION AND THEIR USE FOR INFLUENCING THE BLOOD FLOW

[76] Inventors: Carlos Sunkel, Almarza, 47, Madrid, Spain, 28033; Miguel Fau De Casa-Juana, Torquemada, 17, Madrid, Spain, 28043; Luis Santos, Conde de Pañalver, 32, Madrid, Spain, 28006; Salvador Alonso, Ramón Carrión 9, Madrid, Spain, 28002; Antonio Garcia, Nogales, 141, Madrid, Spain, 28043; Jaime Priego, Avda. Moratalaz, 66, Madrid, Spain, 28030

[21] Appl. No.: 396,214

[22] Filed: Feb. 28, 1995

Related U.S. Application Data

[63] Continuation of Ser. No. 287,944, Aug. 9, 1994, abandoned, which is a continuation of Ser. No. 194,205, Feb. 9, 1994, abandoned, which is a continuation of Ser. No. 104,213, Aug. 9, 1993, abandoned, which is a continuation of Ser. No. 014,428, Feb. 5, 1993, abandoned, which is a continuation of Ser. No. 926,127, Jun. 24, 1991, abandoned.

[51] Int. Cl.$^6$ .................... A61K 31/44; C07D 417/12
[52] U.S. Cl. .......................... 514/338; 546/271.1
[58] Field of Search .................. 546/271.1; 514/338

[56] References Cited

FOREIGN PATENT DOCUMENTS 4003541  8/1991  Germany.

*Primary Examiner*—Jane Fan
*Attorney, Agent, or Firm*—Darby & Darby

[57] ABSTRACT

The invention relates to new 1,4-dihydropyridine derivatives of the general formula I

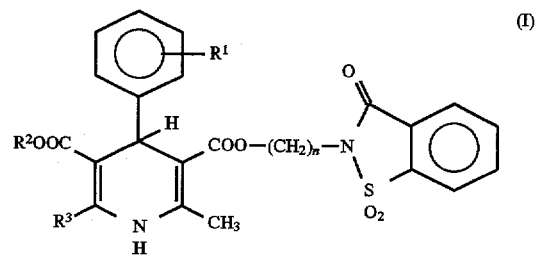

in which $R^1$, $R^2$, $R^3$ and n have the meaning stated in the patent claims.

The compounds of the invention have a vasodilatory effect and are therefore suitable for the treatment of hypertension. Some of the compounds have a vasoconstrictory effect and can therefore be used for the treatment of hypotension.

7 Claims, No Drawings

1,4-DIHYDROPYRIDINE DERIVATIVES, A PROCESS FOR THEIR PREPARATION AND THEIR USE FOR INFLUENCING THE BLOOD FLOW

This patent application is a continuation of patent application Ser. No. 8/287,944 filed Aug. 9, 1994 now abandoned which is a continuation of Ser. No. 8/194,205 filed Feb. 9, 1994 now abandoned which is a continuation of Ser. No. 8/104,213 filed Aug. 9, 1993 now abandoned which is a continuation of Serial No. 8/014,428 filed Feb. 5, 1993 now abandoned which is a continuation of Ser. No. 7/926,127 filed Jun. 24, 1991 now abandoned.

The present invention relates to new 1,4-dihydropyridine derivatives, a process for their preparation and their use as pharmaceutical compositions, in particular for regulating blood pressure and acting on blood flow.

Certain 1,4-dihydropyridine derivatives possess interesting pharmacological properties as coronary and antihypertensive active agents. They have vasodilatory effects and cause an increase in the blood flow in various regions of the vascular system; see F. Bossert and W. Vater, Naturwissenschaften Vol. 58 (1971), p. 578. On the other hand, compounds which are vasoconstrictors and antihypotonics could be obtained by the structural modification of such 1,4-dihydropyridines; see DE-A-27 52 820.

The search for new 1,4-dihydropyridines with a more potent and longer effectiveness and without the undesirable side effects and for new ways of therapeutic application of such compounds is still under way. A modification of the chemical structure can lead to an alteration in the physico-chemical properties of the dihydropyridine system and at the same time modify properties such as duration of effectiveness and selectivity.

A large number of patients suffering from angina pectoris or arrhythmias and changes in the blood pressure could be treated successfully with diuretics and/or β-blockers. These pharmaceutical compositions have the disadvantage, however, that they cannot fully correct the basic hemodynamic disturbance, i.e. the increased peripheral vascular resistance. On the other hand, presently developed 1,4-dihydropyridine derivatives are able to reduce peripheral vascular resistance as potent vasodilators.

The need still exists to avoid the reflex reactions of such agents which could wipe out the benefit of blood pressure reduction, namely angina pectoris due to an increased heart rate.

A new compound for a potential pharmaceutical composition should therefore avoid a high level of cardiac depression and the negative inotropy must therefore be established either in vitro or in vivo.

Various authors claim an increased use of these pharmaceutical compositions for the treatment of hypertension on the basis of their greater vascular than cardiac selectivity and their relatively few side effects. Their effectiveness in the case of young hypertension patients with a high plasma renin level is therefore limited and they often produce headaches, edema, reflex tachycardia and cardio-depression; see J. G. Lewis, "Adverse reactions to calcium antagonists", Drugs Vol. 25 (1983), p. 196 to 222.

Furthermore, chronic treatment of hypertension is accompanied by poor compliance, especially in elderly people, a situation which is aggravated by the multiple daily dosage with the pharmaceutical compositions presently available.

It is therefore the object of the invention to provide new compounds which have a higher vascular than cardiac selectivity and a longer effectiveness and therefore allow a once-a-day therapeutic application. This object is achieved by the invention.

The invention therefore relates to new 1,4-dihydropyridine derivatives according to claims 1 and 2.

The compounds of the invention have a potent and long vasodilatory effect, show a higher vascular than cardiac selectivity and hardly have any side effects. The compound in example 53 has vasoconstrictory properties.

Particular examples of group $R^2$ in the compounds of formula I under the meaning of saturated, branchless or branched $C_1$–$C_8$-alkyl are methyl, ethyl, n-propyl, isopropyl, n-butyl and tert. butyl. Furthermore $R^2$ is a group of the formula W—O—Z in which W is branchless $C_1$–$C_3$-alkylene such as methylene, ethylene or propylene and Z is branchless $C_1$–$C_3$-alkyl, for example methyl, ethyl or propyl.

The compounds of the invention can be prepared according to methods known per se, for example, by reacting a) a compound of the general formula (II)

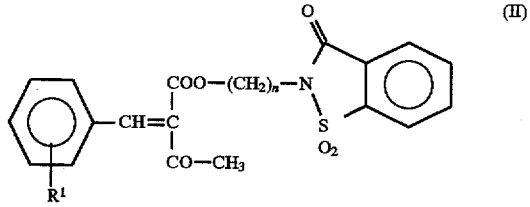

(II)

in which $R^1$ and n are defined as in claim 1 with a compound of the general formula (III)

(III)

in which $R^2$ and $R^3$ are defined as in claim 1 to form the compound of the general formula (I); or b) a compound of the general formula (IV)

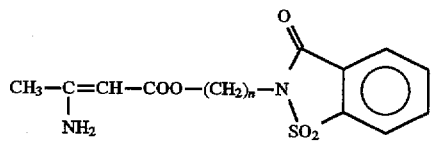

(IV)

in which n is defined as above with a compound of the general formula (V)

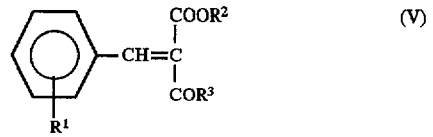

(V)

in which $R^1$, $R^2$ and $R^3$ are defined as above to form a compound of the general formula (I); or c) a compound of the general formula (VI)

(VI)

in which $R^2$ and $R^3$ are defined as above with a compound of the general formula (IV) in which n is defined as above and with a compound of the general formula (VII)

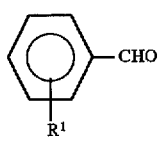

in which R¹ is defined as above to form a compound of the general formula (I); or d) a compound of the general formula (VIII)

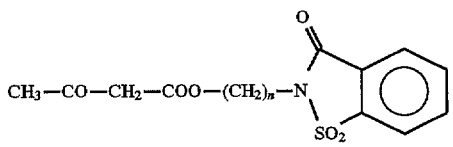

in which n is defined as above with a compound of the general formula (III) in which R² and R³ are defined as above and a compound of the general formula (VII) in which R¹ is defined as above to form a compound of the general formula (I); or e) a compound of the general formula (VI) in which R² and R³ are defined as above with a compound of the general formula (VIII) in which n is defined as above and with a compound of the general formula (VII) in which R¹ is defined as above in the presence of ammonia to form a compound of the general formula (I).

The invention further relates to the separate steps of the preparation of the compounds, for example the steps which start from an intermediate product which is obtained in one of the processes of preparation described above, and the steps of the process which give rise to said intermediate products. Furthermore the invention relates to the salts of the intermediate and final products.

Should mixtures of diastereoisomers or enantiomers be obtained these can be separated in a manner known per se on the basis of the various physico-chemical properties of the components, for example by fractional crystallization and/or chromatography, by reaction with asymmetric reagents or by using microorganisms.

The starting compounds are known or can be obtained by processes known per se in the case that they are new.

The compounds of the invention can be formed as pharmaceutical compositions for oral or rectal administration. For this, the compounds of formula I are combined with physiologically acceptable carriers, inactive ingredients and additives. Consequently the pharmaceutical compositions according to claims 4 to 6 are also subject-matter of the present application. Examples of suitable pharmaceutical forms are tablets, coated tablets, capsules and suppositories as well as fluid forms such as syrups and juices. The quantity of the active ingredient is normally in the range of 0.1 to 99 weight percent of the preparation, preferably from 20 to 50 weight percent in the case of orally administered preparations.

The daily dosage of the active ingredient depends on the mode of administration. In general, 50 to 100 mg per day is administered orally.

The examples illustrate the invention without limiting it. The tests on the pharmacological activity of the compounds can be found after the examples.

EXAMPLE 1

2,6-Dimethyl-5-methoxycarbonyl-4-(3-nitrophenyl)-1,4-dihydropyridine-3-carboxylic acid-2-[N-(1,2-benzisothiazolyl-3(2H)one-1,1-dioxide)]-ethylester A mixture of 15 g (0.05M) of acetyl acetic acid-2-[N-(1,2-benzisothiazolyl-3(2H)one-1,1-dioxide)]-ethylester, 5.55 g (0.05M) of 3-amino crotonic acid methylester and 7.28 g (0.05M) of nitrobenzaldehyde is heated at reflux and stirred in 50 ml of absolute ethanol for 10 hours. Cooling of the resulting solution to room temperature gives a yellow solid having a melting point of 179° to 182° C. (recrystallized from ethanol). The yield is 67%.

EXAMPLE 2

2,6-Dimethyl-5-ethoxycarbonyl-4-(3-nitrophenyl)-1,4-dihydropyridine-3-carboxylic acid-2-[N-(1,2-benzisothiazolyl-3(2H)one-1,1-dioxide)]-ethylester A mixture of 15 g (0.05M) of acetyl acetic acid-2-[N-(1,2-benzisothiazolyl)-3(2H) one-1,1-dioxide)]-ethylester, 6.22 g (0.05M) of 3-amino crotonic acid ethylester and 7.28 g (0.05M) of 3-nitrobenzaldehyde is heated at reflux and stirred in 50 ml of absolute ethanol for 10 hours. Removal of 40 ml of solvent by distillation under reduced pressure gives a yellow solid having a melting point of 89° to 91° C. The yield is 87%.

EXAMPLE 3

2,6-Dimethyl-5-isopropoxycarbonyl-4-(3-nitrophenyl)-1,4-dihydropyridine-3-carboxylic acid-2-[N-(1,2-benzisothiazolyl-3(2H)one-1,1-dioxide)]-ethylester A) 2-(3-Nitrobenzylidene)-acetyl acetic acid-2-[N-[1,2-benzisothiazolyl-3(2H)one-1,1-dioxide)]-ethylester A mixture of 500 g (1.61M) of acetyl acetic acid-2-[N-(1,2-benzisothiazolyl-3(2H)one-1,1-dioxide)]-ethylester, 242.72 g (1.61M) of 3-nitrobenzaldehyde, 7.3 ml of piperidine and 19.5 ml of glacial acetic acid is kept in 1.5 l of anhydrous isopropanol at 40° C. for 1 hour with stirring, then at room temperature for 16 hours and finally at 0° C. for 2 hours. After that time the resulting suspension is cooled overnight to −10° C. to give a yellow solid having a melting point of 145° to 147° C. (recrystallized from ethyl acetate). The yield is 85%.

B) 2,6-Dimethyl-5-isopropoxycarbonyl-4-(3-nitrophenyl)-1,4-dihydropyridine-3-carboxylic acid-2-[N-(1,2-benzisothiazolyl-3(2H)one-1,1-dioxide)]-ethylester A mixture of 15 g (0.03M) of 2-(3-nitrobenzylidene)-acetyl acetate acid-2-[N-(1,2-benzisothiazolyl-3(2H)one-1,1-dioxide)]-ethylester and 4.85 g (0.03M) of 3-amino crotonic acid isopropylester is heated at reflux and stirred in 35 ml of absolute ethanol for 10 hours. After that time the resulting solution is cooled to 0° C. and the solvent decanted. This results in a product which is dissolved in 10 ml of boiling ethyl acetate and then maintained at room temperature with stirring until solidification is completed to give a crystalline yellow solid in the form of prisms having a melting point of 121° to 123° C. (recrystallized from methanol). The yield is 70%.

EXAMPLE 4

2,6-Dimethyl-5-ethoxycarbonyl-4-(3-nitrophenyl)-1,4-dihydropyridine-3-carboxylic acid-N-(1,2-benzisothiazolyl-3-(2H)one-1,1-dioxide )-methylester A mixture of 15 g (0.05M) of acetyl acetic acid-N-(1,2-benzisothiazolyl-3(2H)one-1,1-dioxide)-methylester, 6.52 g (0.05M) of 3-amino crotonic acid ethylester and 7.62 g (0.05M) of 3-nitrobenzaldehyde is heated at reflux and stirred in 50 ml of absolute ethanol for 8 hours. Cooling of the reaction mixture to −10° C. for 12 hours and subsequent stirring at room temperature gives a yellow solid having a melting point of 186° to 188° C. (recrystallized from ethanol). The yield is 40%.

EXAMPLE 5

2,6-Dimethyl-5-methoxycarbonyl-4-(2-nitrophenyl)-1,4-dihydropyridine-3-carboxylic acid-N-(1,2-benzisothiazolyl-3(2H)one-1,1-dioxide)-methylester A) 2-(2-Nitrobenzylidene)-acetyl acetic acid-N-(1,2-benzisothiazolyl-3(2H)one-1,1-dioxide)-methylester A mixture of 50 g (0.33M) of 2-nitrobenzaldehyde, 98.36 g (0.33M) of acetyl acetic acid-N-(1,2-benzisothiazolyl-3(2H)one-1,1-dioxide)-methylester, 1.5 ml of piperidine and 4 ml of glacial acetic acid in 620 ml of anhydrous isopropanol is maintained at 50° C. for 10 hours with stirring vigorously. After that time the resulting suspension is cooled overnight to −10° C. to give a yellow solid having a melting point of 140° to 141° C. (recrystallized from ethyl acetate). The yield is 65%.

B) 2,6-Dimethyl-5-methoxycarbonyl-4-(2-nitrophenyl)-1,4-dihydropyridine-3-carboxylic acid-N-(1,2-benzisothiazolyl-3(2H)one-1,1-dioxide)-methylester A mixture of 15 g (0.03M) of 2-(2-nitrobenzylidene)-acetyl acetic acid-N-(1,2-benzisothiazolyl-3(2H)one-1,1-dioxide)methylester (obtained as described in paragraph A above) and 4.91 g (0.03M) of 3-amino crotonic acid methylester is heated at reflux and stirred in 40 ml of absolute ethanol for 10 hours. After that time the solvent is removed by distillation under reduced pressure and the residue dissolved in 20 ml of boiling ethyl acetate and allowed to cool down slowly to give a yellow solid having a melting point of 242° to 244° C. (recrystallized from ethyl acetate). The yield is 75%.

EXAMPLE 6

2,6-Dimethyl-5-(2-methoxyethoxycarbonyl)-4-(2-nitrophenyl)-1,4-dihydropyridine-3-carboxlic acid-N-(1,2-benzisothiazolyl-3(2H)one-1,1-dioxide)-methylester A mixture of 15 g (0.03M) of 2-(2-nitrobenzylidene)-acetyl acetic acid-N-(1,2-benzisothiazolyl-3(2H)one-1,1-dioxide)methylester (obtained as described in Example 5) and 5.55 g (0.03M) of 3-amino crotonic acid-2-methoxyethylester is heated at reflux and stirred in 40 ml of absolute ethanol for 10 hours. After that time the reaction mixture is slowly cooled to room temperature to give a yellow solid having a melting point of 180° to 182° C. (recrystallized from ethyl acetate). The yield is 67%.

EXAMPLE 7

2,6-Dimethyl-5-(2-methoxyethoxycarbonyl)-4-(3-nitrophenyl)-1,4-dihydropyridine-3-carboxylic acid-N-(1,2-benzisothiazolyl-3-(2H)one-1,1-dioxide)-methylester A mixture of 15 g (0.05M) of acetyl acetic acid-N-(1,2-benzisothiazolyl-3(2H)one-1,1-dioxide)-methylester, 8.03 g (0.05M) of 3-amino crotonic acid-2-methoxyethylester and 7.62 g (0.05M) of 3-nitrobenzaldehyde is heated at reflux and stirred in 50 ml of isopropanol for 16 hours. After that time the reaction mixture is cooled to room temperature to give a yellow solid having a melting point of 164° to 165° C. (recrystallized from ethyl acetate). The yield is 76%.

EXAMPLE 8

4-(2,3-Dichlorophenyl)-2,6-dimethyl-5-methoxycarbonyl-1,4-dihydropyridine-3-carboxylic acid-2-[N-(1,1-benzisothiazolyl-3(2H)-one-1,1-dioxide)]-ethylester A mixture of 15 g (0.05M) of acetyl acetic acid-2-[N-(1,2-benzisothiazolyl-3(2H)one-1,1-dioxide)]-ethylester, 5.55 g (0.05M) of 3-amino crotonic acid methylester and 8.43 g (0.05M) of 2,3-dichlorobenzaldehyde is heated at reflux and stirred in 50 ml of absolute ethanol for 10 hours. After that time the mixture is cooled to 0° C. and maintained at that temperature for 5 hours with stirring to give a yellow solid having a melting point of 172° to 175° C. (recrystallized from ethanol). The yield is 66%.

EXAMPLE 9

2,6-Dimethyl-5-(2-methoxyethoxycarbonyl)-4-(3-nitrophenyl)-1,4-dihydropyridine-3-carboxylic acid-2-[N-(1,2-benzisothiazolyl-3(2H)one-1,1-dioxide)]-ethylester A mixture of 15 g (0.03M) of 2-(3-nitrobenzylidene)-acetyl acetic acid-2-[N-(1,2-benzisothiazolyl-3(2H)one-1,1-dioxide)]-ethylester (obtained as described in Example 3) and 5.37 g (0.03M) of 3-amino crotonic acid-2-methoxyethylester is heated at reflux and stirred in 40 ml of absolute ethanol for 10 hours. After that time the reaction mixture is cooled to −10° C., the solvent decanted and the residue in the form of oil is first subjected to heat treatment with 200 ml of a 1:1 mixture of ethyl acetate and n-hexane and then maintained at room temperature with stirring until solidification of the product is completed to give a yellow solid having a melting point of 126° to 128° C. The yield is 51%.

EXAMPLE 10

2,6-Dimethyl-5-methoxycarbonyl-4-(3-nitrophenyl)-1,4-dihydropyridine-3-carboxylic acid-N-(1,2-benzisothiazolyl-3-(2H)one-1,1-dioxide)-methylester A mixture of 15 g (0.05M) of acetyl acetic acid-N-(1,2-benzisothiazolyl-3(2H)one-1,1-dioxide)-methylester, 5.81 g (0.05M) of 3-amino crotonic acid methylester and 7.62 g (0.05M) of 3-nitrobenzaldehyde is heated at reflux and stirred in 50 ml of absolute ethanol for 10 hours. After that time the reaction mixture is stirred at room temperature for 4 hours and then the resulting solid dissolved in 600 ml of boiling ethanol. Thereafter the resulting solution is cooled to room temperature, the precipitated solid filtered off and the filtrate concentrated to ⅓ of its volume to give a yellow solid having a melting point of 187° to 188° C. (recrystallized from ethanol). The yield is 43%.

EXAMPLE 11

4-(2,3-Dichlorophenyl)-2,6-dimethyl-5-(2-methoxyethoxycarbonyl)-1,4-dihydropyridine-3-carboxylic acid-N-(1,2-benzisothiazolyl-3(2H)one-1,1-dioxide)-methylester A mixture of 15 g (0.05M) of acetyl acetic acid-N-(1,2-benzisothiazolyl-3(2H)one-1,1-dioxide)-methylester, 8.03 g (0.05M) of 3-amino crotonic acid-2-methoxyethylester and 8.83 g (0.05M) of 2,3-dichlorobenzaldehyde is heated at reflux and stirred in 50 ml of absolute ethanol for 10 hours. After that time the reaction mixture is cooled to −10° C., the supernatant liquid decanted and the residue in the form of oil dissolved in 15 ml of boiling ethyl acetate.

Finally the solution is stirred at room temperature until solidification of the product is completed to give a yellow solid having a melting point of 166° to 167° C. (recrystallized from ethyl acetate). The yield is 68%.

EXAMPLE 12

2,6-Dimethyl-5-isopropoxycarbonyl-4-(2-nitrophenyl)-1,4-dihydropyridine-3-carboxylic acid-N-(1,2-benzisothiazolyl-3(2H)one-1,1-dioxide)-methylester A mixture of 15 g (0.03M) of 2-(2-nitrobenzylidene)-acetyl acetic acid-N-(1,2-benzisothiazolyl-3(2H)one-1,1-dioxide)-methylester (obtained as described in Example 5) and 4.99 g (0.03M) of 3-amino crotonic acid isopropylester is heated at reflux and stirred in 40 ml of absolute ethanol for 10 hours. After that time the reaction mixture is slowly cooled to room temperature to give a yellow solid having a melting point of 176° to 178° C. (recrystallized from ethanol). The yield is 79%.

EXAMPLE 13

4-(2,3-Dichlorophenyl)-2,6-dimethyl-5-methoxycarbonyl-1,4-dihydropyridine-3-carboxylic acid-N-(1,2-benzisothiazolyl-3(2H)one-1,1-dioxide)-methylester A mixture of 15 g (0.05M) of acetyl acetic acid-N-(1,2-benzisothiazolyl-3(2H) one-1,1-dioxide)-methylester, 5.81 g (0.05M) of 3-amino crotonic acid methylester and 8.83 g (0.05M) of 2,3-dichlorobenzaldehyde is heated at reflux and stirred in 50 ml of absolute ethanol for 12 hours. After that time the reaction mixture is cooled to −10° C., the liquid supernatant decanted and the residue dissolved in 10 ml of boiling methanol. Finally the resulting solution is stirred at room temperature until solidification of the product is completed to give a solid having a melting point of 204° to 206° C. which crystallizes with half a molecule of ethanol upon recrystallization from ethanol. The yield is 70%.

EXAMPLE 14

2,6-Dimethyl-5-(2-methoxyethoxycarbonyl)-4-(2-trifluoromethylphenyl)-1,4-dihydropyridine-3-carboxylic acid-2-[N-(1,2-benzisothiazolyl-3(2H) one-1,1-dioxide)]-ethylester A) 2-(2-Trifluoromethylbenzylidene)-acetyl acetic acid-2-[N-(1,2-benzisothiazolyl-3(2H)one-1,1-dioxide)]-ethylester A mixture of 50 ml (66 g; 0.38M) of 2-trifluoromethylbenzaldehyde, 118 g (0.38M) of acetyl acetic acid-2-[N-(1,2-benzisothiazolyl-3(2H)one-1,1-dioxide)]-ethylester, 1.7 ml of piperidine and 4.6 ml of glacial acetic acid is kept in 355 ml of anhydrous isopropanol at 40° C. for 1 hour with stirring, then at room temperature for 16 hours and finally at 0° C. for 2 hours. After that time the resulting suspension is cooled overnight to −10° C. to give a yellow solid having a melting point of 135° to 137° C. (recrystallized from ethanol). The yield is 87%.

B) 2,6-Dimethyl-5-(2-methoxyethoxycarbonyl)-4-(2-trifluoromethylphenyl)-1,4-dihydropyridine-3-carboxylic acid-2-[N-(1,2-benzisothiazolyl-3(2H) one-1,1-dioxide)]-ethylester A mixture of 15 g (0.03M) of 2-(2-trifluoromethylbenzylidene)-acetyl acetic acid-2-[N-(1,2-benzisothiazolyl-3(2H)one-1,1-dioxide)]-ethylester and 5.27 g (0.03M) of amino crotonic acid-2-methoxyethylester is heated at reflux and stirred in 35 ml of absolute ethanol for 24 hours. After that time the reaction mixture is cooled to 0° C. to give a yellow solid having a melting point of 140° to 142° C. (recrystallized from ethanol). The yield is 81%.

EXAMPLE 15

4-(2,3-Dichlorophenyl)-2,6-dimethyl-5-ethoxycarbonyl-1,4-dihydropyridine-3-carboxylic acid-2-[N-(1,2-benzisothiazolyl-3(2H)one-1,1-dioxide)]-ethylester A) 2-(2,3-Dichlorobenzylidene)-acetyl acetic acid-2-[N-(1,2-benzisothiazolyl-3(2H)one-1,1-dioxide)]-ethylester A mixture of 50 g (0.29M) of 2,3-dichlorobenzaldehyde, 88.94 g (0.29M) of acetyl acetic acid-2-[N-(1,2-benzisothiazolyl-3(2H)one-1,1-dioxide)]-ethylester, 1.3 ml of piperidine and 3.5 ml of glacial acetic acid is kept in 270 ml of anhydrous isopropanol at 40° C. for 1 hour with stirring, then at room temperature for 16 hours and finally, at 0° C. for 2 hours. After that time the resulting suspension is cooled overnight to −10° C. to give a yellow solid having a melting point of 114° to 116° C. The yield is 95%.

B) 4-(2,3-Dichlorophenyl)-2,6-dimethyl-5-ethoxycarbonyl-1,4-dihydropyridine-3-carboxylic acid-2-[N-(1,2-benzisothiazolyl-3(2H)one-1,1-dioxide)]-ethylester A mixture of 15 g (0.03M) of 2-(2,3-dichlorobenzylidene)-acetyl acetic acid-2-[N-(1,2-benzisothiazolyl-3(2H)one-1,1-dioxide)]-ethylester and 4.14 g (0.03M) of 3-amino crotonic acid ethylester is heated at reflux and stirred in 35 ml of absolute ethanol for 24 hours. After that time the reaction mixture is slowly cooled to room temperature to give a pale yellow solid having a melting point of 177° to 178° C. (recrystallized from ethanol). The yield is 79%.

EXAMPLE 16

4-(2,3-Dichlorophenyl)-2,6-dimethyl-5-isopropoxycarbonyl-1,4-dihydropyridine-3-carboxyic acid-2-[N-(1,2-benzisothiazolyl-3(2H) one-1,1-dioxide)]-ethylester A mixture of 7.9 g (0.02M) of 2-(2,3-dichlorobenzylidene)-acetyl acetic acid-2[N-(1,2-benzisothiazolyl-3(2H)one-1,1-dioxide)]-ethylester (obtained as described in Example 15) and 2.42 g (0.02M) of 3-amino crotonic acid isopropylester is heated at reflux and stirred in 20 ml of absolute ethanol for 20 minutes. After that time the reaction mixture is slowly cooled to room temperature to give a pale yellow solid having a melting point of 194° to 195° C. (recrystallized from ethanol). The yield is 79%.

EXAMPLE 17

2,6-Dimethyl-5-ethoxycarbonyl-4-(2-trifluoromethylphenyl)-1,4-dihydropyridine-3-carboxylic acid-2-[N-(1,2-benzisothiazolyl-3(2H) one-1,1-dioxide)]-ethylester A mixture of 15 g (0.03M) of 2-(2-trifluoromethylbenzylidene)-acetyl acetic acid-2-[N-(1,2- benzisothiazolyl-3(2H)one-1,1-dioxide)]-ethylester (obtained as described in Example 14) and 4.14 g (0.03M) of 3-amino crotonic acid ethylester is heated at reflux and stirred in 70 ml of anhydrous isopropanol for 20 hours. After that time the reaction mixture is cooled to −10° C., the supernatant liquid decanted and the residue in the form of oil dissolved in 15 ml of boiling ethyl acetate. Finally the resulting solution is stirred at room temperature until solidification of the product is completed to give a pale yellow solid having a melting point of 147° to 148° C. (recrystallized from ethanol). The yield is 76%.

EXAMPLE 18

2,6-Dimethyl-5-isopropoxycarbonyl-4-(2-trifluoromethylphenyl)-1,4-dihydropyridine-3-carboxylic acid-2-[N-(1,2-benzisothiazolyl-3(2H)one-1,1-dioxide)]-ethylester A mixture of 15 g (0.03M) of 2-(2-trifluoromethylbenzylidene)-acetyl acetic acid-2-[N-(1,2-benzisothiazolyl-3(2H)one-1,1-dioxide)]-ethylester (obtained as described in Example 14) and 4.6 g (0.03M) of 3-amino crotonic acid isopropylester is heated at reflux and stirred in 35 ml of absolute ethanol for 20 hours. After that time 15 ml of solvent are removed by distillation under reduced pressure and the resulting solution is cooled overnight to −10° C. to give a white solid having a melting point of 146° to 147° C. (recrystallized from ethyl acetate). The yield is 77%.

EXAMPLE 19

4-(2-Chlorophenyl)-2,6-dimethyl-5-ethoxycarbonyl-1,4-dihydropyridine-3-carboxylic acid-2-[N-(1,2-benzisothiazolyl-3(2H)one-1,1-dioxide)]-ethylester A) 2-(2-Chlorobenzylidene)-acetyl acetic acid-2-[N-(1,2-benzisothiazolyl-3(2H)one-1,1-dioxide)]-ethylester A mixture of 60 ml (74.88 g; 0.53M) of 2-chlorobenzaldehyde, 165.83 g (0.53M) of acetyl acetic acid-2-[N-(1,2-benzisothiazolyl-3(2H)one-1,1-dioxide)]-ethylester, 2.4 ml of piperidine and 6.4 ml of glacial acetic acid is stirred in 500 ml of anhydrous isopropyl alcohol at 40° C. for 1 hour, then at room temperature for 16 hours and finally at 0° C. for 2 hours. After that time the resulting suspension is cooled overnight to −10° C. to give a light yellow solid having a melting point of 163° to 165° C. The yield is 92%.

B) 4-(2-Chlorophenyl)-2,6-dimethyl-5-ethoxycarbonyl-1,4-dihydropyridine-3-carboxylic acid-2-[N-(1,2-benzisothiazolyl-3(2H)one-1,1-dioxide)]-ethylester A mixture of 15 g (0.03M) of 2-(2-chlorobenzylidene)-acetyl acetic acid-2-[N-(1,2-benzisothiazolyl-3(2H)one-1,1-dioxide)]-ethylester and 4.47 g (0.03M) of 3-amino crotonic acid ethylester is heated at reflux and stirred in 35 ml of anhydrous isopropanol for 24 hours. After that time the reaction mixture is cooled to room temperature to give a yellow solid having a melting point of 168° to 170° C. (recrystallized from ethanol). The yield is 65%.

EXAMPLE 20

2,6-Dimethyl-5-methoxycarbonyl-4-(2-trifluoromethylphenyl)-1,4-dihydropyridine-3-carboxylic acid-2-[N-(1,2-benzisothiazolyl-3(2H)one-1,1-dioxide)]-ethylester A mixture of 15 g (0.03M) of 2-(2-trifluoromethylbenzylidene)-acetyl acetic acid-2-[N-(1,2-benzisothiazolyl-3(2H)one-1,1-dioxide)]-ethylester (obtained as described in Example 14) and 3.69 g (0.03M) of 3-amino crotonic acid methylester is heated at reflux and stirred in 35 ml of absolute ethanol for 20 hours. After that time the reaction mixture is slowly cooled to room temperature to give a yellow solid having a melting point of 195° to 197° C. (recrystallized from ethanol). The yield is 78%.

EXAMPLE 21

4-(2-Chlorophenyl)-2,6-dimethyl-5-(2-methoxyethoxycarbonyl)-1,4-dihydropyridine-3-carboxylic acid-2-[N-(1,2-benzisothiazolyl-3(2H)-one-1,1-dioxide)]-ethylester A mixture of 15 g (0.03M) of 2-(2-chlorobenzylidene)-acetyl acetic acid-2-[N-(1,2-benzisothiazolyl-3(2H)-one-1,1-dioxide)]-ethylester (obtained as described in Example 19) and 5.5 g (0.03M) of 3-amino crotonic acid-2-methoxyethylester is heated at reflux and stirred in 40 ml of absolute ethanol for 24 hours. After that time the solvent is removed by distillation under reduced pressure and the resulting residue dissolved in 10 ml of boiling ethyl acetate. Finally the resulting solution is stirred at room temperature until solidification of the product is completed to give a yellowish solid having a melting point of 128° to 130° C. (recrystallized from ethanol). The yield is 60%.

EXAMPLE 22

4-(2,3-Dichlorophenyl)-2,6-dimethyl-5-(2-methoxyethoxycarbonyl)-1,4-dihydropyridine-3-carboxylic acid-2-[N-(1,2-benzisothiazolyl-3(2H)one-1,1-dioxide)]-ethylester A mixture of 10 g (0.02M) of 2-(2,3-dichlorobenzylidene) acetyl acetic acid-2[N-(1,2-benzisothiazolyl)-3(2H)one-1,1-dioxide)]-ethylester (obtained as described in Example 15) and 3.4 g (0.02M) of 3-amino crotonic acid-2-methoxyethylester is heated at reflux and stirred in 25 ml of absolute ethanol for 20 hours. After that time the reaction mixture is cooled to −10° C., the liquid supernatant decanted and the residue dissolved in 15 ml of boiling ethyl acetate. Finally the resulting solution is cooled to 5° C. to give a solid having a melting point of 153° to 156° C. (recrystallized from ethanol). The yield is 46%.

EXAMPLE 23

4-(2-Chlorophenyl)-2,6-dimethyl-5-isopropoxycarbonyl-1,4-dihydropyridine-3-carboxylic acid-2-[N-(1,2-benzisothiazolyl-3(2H)one-1,1-dioxide)]-ethylester A mixture of 15 g (0.03M) of 2-(2-chlorobenzylidene)-acetyl acetic acid-2-[N-(1,2-benzisothiazolyl-3(2H)one-1,1-dioxide)]-ethylester (obtained as described in Example 19) and 4.95 g (0.03M) of 3-amino crotonic acid isopropylester is heated at reflux and stirred in 160 ml of absolute ethanol for 24 hours. After that time the reaction mixture is cooled to room temperature to give a yellow solid having a melting point of 186° to 187° C. (recrystallized from ethyl acetate). The yield is 75%.

EXAMPLE 24

4-(2-Chlorophenyl)-2,6-dimethyl-5-methoxycarbonyl-1,4-dihydropyridine-3-carboxylic acid-2-[N-(1,2-benzisothiazolyl-3(2H)one-1,1-dioxide)]-ethylester A mixture of 15 g (0.03M) of 2-(2-chlorobenzylidene)-acetyl acetic acid-2-[N-(1,2-benzisothiazolyl-3(2H)one-1,1- dioxide)]-ethylester (obtained as described in Example 19) and 3.98 g (0.03M) of 3-amino crotonic acid methylester is heated at reflux and stirred in 80 ml of absolute ethanol for 24 hours. After that time the reaction mixture is first cooled overnight to −10° C. and then stirred at room temperature until solidification of the product is completed to give a solid having a melting point of 160° to 162° C. (recrystallized from ethyl acetate). The yield is 67%.

EXAMPLE 25

2,6-Dimethyl-5-isopropoxycarbonyl-4-(3-nitrophenyl)-1,4-dihydropyridine-3-carboxylic acid-3-[N-(1,2-benzisothiazolyl-3(2H)one-1,1-dioxide)]-propylester A mixture of 15 g (0.05M) of acetyl acetic acid-3-[N-(1, 2-benzisothiazolyl-3(2H)one-1,1-dioxide)]-propylester, 6.97 g (0.05M) of 3-nitrobenzaldehyde and 6.6 g (0.05M) of 3-amino crotonic acid isopropylester is heated at reflux and stirred in 50 ml of absolute ethanol for 8 hours. After that time the reaction mixture is cooled to room temperature to give a yellow solid having a melting point of 181° to 183° C. (recrystallized from ethyl acetate). The yield is 64%.

EXAMPLE 26

2,6-Dimethyl-5-ethoxycarbonyl-4-(3-nitrophenyl)-1,4-dihydropyridine-3-carboxylic acid-3-[N-(1,2-benzisothiazolyl-3(2H)one-1,1-dioxide)]-propylester A mixture of 15 g (0.05M) of acetyl acetic acid-3-[N-(1, 2-benzisothiazolyl-3(2H)one-1,1-dioxide)]-propylester, 6.97 g (0.05 Mol) of 3-nitrobenzaldehyde and 6 g (0.05M) of 3-amino crotonic acid ethylester is heated at reflux and stirred in 50 ml of absolute ethanol for 8 hours. After that time the reaction mixture is cooled to 0° C. and stirred at this temperature until solidification of the product is completed to give a yellow solid having a melting point of 143° to 145° C. (recrystallized from ethanol). The yield is 55%.

EXAMPLE 27

2,6-Dimethyl-5-methoxycarbonyl-4-(3-nitrophenyl)-1,4-dihydropyridine-3-carboxylic acid-3-[N-(1,2-benzisothiazolyl-3(2H)one-1,1-dioxide)]-propylester A mixture of 15 g (0.05M) of acetyl acetic acid-3-[N-1, 2-benzisothiazolyl-3(2H)one-1,1-dioxide)]-propylester, 6.97 g (0.05M) of 3-nitrobenzaldehyde and 5.31 g (0.05M) of 3-amino crotonic acid methylester is heated at reflux and stirred in 50 ml of absolute ethanol for 8 hours. After that time the reaction mixture is cooled to room temperature to give a yellow solid having a melting point of 185° to 188° C. which crystallizes with half a molecule of ethanol upon recrystallization from ethanol. The yield is 70%.

EXAMPLE 28

2,6-Dimethyl-5-(2-methoxyethoxycarbonyl)-4-(3-nitrophenyl)-1,4-dihydropyridine-3-carboxylic acid-3-[N-(1,2-benzisothiazolyl-3(2H)one-1,1-dioxide)]-propylester A mixture of 15 g (0.05M) of acetyl acetic acid-3-[N-(1, 2-benzisothiazolyl-3(2H)one-1,1-dioxide)]-propylester, 6.97 g (0.05M) of 3-nitrobenzaldehyde and 7.34 g (0.05M) of 3-amino crotonic acid-2-methoxyethylester is heated at reflux and stirred in 50 ml of absolute ethanol for 8 hours. After that time the reaction mixture is cooled to −10° C., the supernatant liquid decanted and the residue dissolved in 15 ml of boiling ethyl acetate. Finally the resulting solution is stirred at room temperature until solidification of the product is completed to give a yellow solid having a melting point of 133° to 135° C. (recrystallized from ethyl acetate). The yield is 64%.

EXAMPLE 29

4-(2,3-Dichlorophenyl)-2,6-dimethyl-5-methoxycarbonyl-1,4-dihydropyridine-3-carboxylic acid-3-[N-(1,2-benzisothiazolyl-3(2H)one-1,1-dioxide)]-propylester A mixture of 15 g (0.05M) of acetyl acetic acid-3-[N-(1, 2-benzisothiazolyl-3(2H)one-1,1-dioxide)]-propylester, 8.07 g (0.05M) of 2,3-dichlorobenzaldehyde and 5.31 g (0.05M) of 3-amino crotonic acid methylester is heated at reflux and stirred in 50 ml of absolute ethanol for 18 hours. After that time the reaction mixture is cooled to −10° C., the supernatant liquid decanted and the oily residue dissolved in 15 ml of boiling ethyl acetate. Finally the resulting solution is stirred at room temperature until solidification is completed to give a white solid having a melting point of 173° bis 177° C. (recrystallized from ethanol). The yield is 66%.

EXAMPLE 30

6-Ethyl-2-methyl-5-methoxycarbonyl-4-(3-nitrophenyl)-1,4-dihydropyridine-3-carboxylic acid-2-[N-(1,2-benzisothiazolyl-3(2H)one-1,1-dioxide)]-ethylester A mixture of 15 g (0.03M) of 2-(3-nitrobenzylidene)-ethyl acetate-2-[N-(1,2-benzisothiazolyl-3(2H)one-1,1-dioxide)]-ethylester (obtained as described in Example 3) and 4.36 g (0.03M) of 3-amino-4-methyl crotonic acid methylester is heated at reflux and stirred in 35 ml of absolute ethanol for 8 hours. After that time the reaction mixture is cooled to −10° C., the supernatant liquid decanted and the oily residue dissolved in 10 ml of boiling ethyl acetate. Finally the resulting solution is stirred at room temperature until solidification of the product is completed to give a yellow solid having a melting point of 145° to 147° C. (recrystallized from ethanol). The yield is 81%.

EXAMPLE 31

6-Ethyl-2-methyl-5-methoxycarbonyl-4-(2-trifluoromethylphenyl)-1,4-dihydropyridine-3-carboxylic acid-2-[N-(1,2-benzisothiazolyl)-3(2H) one-1,1-dioxide)]-ethylester A mixture of 15 g (0.03M) of 2-(2-trifluoromethylbenzylidene)-acetyl acetic acid-2-[N-(1,2-benzisothiazolyl-3(2H)one-1,1-dioxide)]-ethylester (obtained as described in Example 14) and 4.14 g (0.03M) of 3-amino-4-methyl crotonic acid methylester is heated at reflux and stirred in 35 ml of absolute ethanol for 14 hours. After that time the reaction mixture is cooled to −10° C. to give a yellow solid having a melting point of 137° to 138° C. (recrystallized from ethyl acetate). The yield is 49%.

EXAMPLE 32

4-(2-Chlorophenyl)-2,6-dimethyl-5-ethoxycarbonyl-1,4-dihydropyridine-3-carboxylic acid-3-[N-(1,2-benzisothiazolyl-3(2H)one-1,1-dioxide)]-propylester A) 2-(2-Chlorobenzylidene)-acetyl acetic acid-3-[N-(1,2-benzisothiazolyl-3(2H)one-1,1-dioxide)]-propylester A mixture of 25 g (0.08M) of acetyl acetic acid-3-[N-(1, 2-benzisothiazolyl-3(2H)one-1,1-dioxide)]-propylester, 8.7 ml (10.8 g; 0.08M) of 2-chlorobenzaldehyde, 0.27 ml of glacial acetic acid and 0.44 ml of piperidine in 50 ml of anhydrous isopropanol is stirred at 40° C. for 1 hour, then at room temperature for 16 hours and finally at 0° C. for 2 hours. Cooling of the resulting reaction mixture overnight to −10° C. gives a yellow-orange solid having a melting point of 66° to 68° C. The yield is 77%.

B) 4-(2-Chlorophenyl)-2,6-dimethyl-5-ethoxycarbonyl-1,4-dihydropyridine-3-carboxylic acid-3-[N-(1,2-benzisothiazolyl-3(2H)one-1,1-dioxide)]-propylester A mixture of 12 g (0.03M) of 2-(2-chlorobenzylidene)-acetyl acetic acid-3-[N-(1,2-benzisothiazolyl-3(2H)one-1,1-dioxide)]-propylester and 3.5 g (0.03M) of 3-amino Crotonic acid ethylester is heated at reflux and stirred for 24 hours in 90 ml of absolute ethanol. After that time the reaction mixture is cooled to room temperature to give a yellowish solid having a melting point 171° to 172° C. (recrystallized from ethanol). The yield is 65%.

EXAMPLE 33

2,6-Dimethyl-5-isopropoxycarbonyl-4-(2-trifluoromethylphenyl)-1,4-dihydropyridine-3-carboxylic acid-3-[N-(1,2-benzisothiazolyl-3(2H) one-1,1-dioxide)]-propylester A) 2-(2-Trifluoromethylbenzylidene)-acetyl acetic acid-3-[N-(1,2-benzisothiazolyl-3(2H)one-1,1-dioxide)]-propylester A mixture of 25 g (0.08M) of acetyl acetic acid-3-[N-(1,2-benzisothiazolyl-3(2H)one-1,1-dioxide)]-propylester, 10.1 ml (13.38 g; 0.08M) of 2-trifluoromethylbenzaldehyde, 0.27 ml of glacial acetic acid and 0.44 ml of piperidine in 50 ml of anhydrous isopropanol is stirred at 40° C. for 1 hour, then at room temperature for 16 hours and finally at 0° C. for 2 hours. After that time the reaction mixture is maintained overnight at −10° C. to give a very dense oil which is separated by decanting and dissolved in 15 ml of boiling ethyl acetate. Finally the resulting solution is stirred at room temperature until solidification of the product is completed to give a white solid having a melting point of 104° to 105° C. The yield is 76%.

B) 2,6-Dimethyl-5-isopropoxycarbonyl-4-(2-trifluoromethylphenyl)-1,4-dihydropyridine-3-carboxylic acid-3-[N-(1,2-benzisothiazolyl-3(2H) one-1,1-dioxide)]-propylester A mixture of 15 g (0.03M) of 2-(2-trifluoromethylbenzylidene)-acetyl acetic acid-(3-[N-(1,2-benzisothiazolyl-3(2H)one-1,1-dioxide)]-propylester and 4.5 g (0.03M) of 3-amino crotonic acid isopropylester is heated at reflux and stirred in 35 ml of absolute ethanol for 18 hours. After that time the reaction mixture is cooled to −10° C. to give a pale yellow solid having a melting point of 175° to 176° C. (recrystallized from ethanol). The yield is 80%.

EXAMPLE 34

4-(2-Chlorophenyl)-2,6-dimethyl-5-methoxycarbonyl-1,4-dihydropyridine-3-carboxylic acid-3-[N-(1,2-benzisothiazolyl-3(2H)one-1,1-dioxide)]-propylester A mixture of 12 g (0.03M) of 2-(2-chlorobenzylidene)-acetyl acetic acid-3-[N-(1,2-benzisothiazolyl-3(2H)one-1,1-dioxide)]-propylester (obtained as described in Example 32) and 3.1 g (0.03M) of 3-amino crotonic acid methylester is heated at reflux and stirred in 60 ml of absolute ethanol for 24 hours. After that time the reaction mixture is cooled to room temperature to give a yellow solid having a melting point of 170° to 171° C. (recrystallized from ethanol). The yield is 66%.

EXAMPLE 35

4-(2,3-Dichlorophenyl)-6-ethyl-2-methyl-5-methoxycarbonyl-1,4-dihydropyridine-3-carboxylic acid-2-[N-(1,2-benzisothiazolyl-3(2H)one-1,1-dioxide)]-ethylester A mixture of 15 g (0.03M) of 2-(2,3-dichlorobenzylidene) acetyl acetic acid-2[N-(1,2-benzisothiazolyl-3(2H)one-1,1-dioxide)]-ethylester (obtained as described in Example 15) and 4.14 g (0.03M) of 3-amino-4-methyl crotonic acid methylester is heated at reflux and stirred in 35 ml of absolute ethanol for 18 hours. After that time the reaction mixture is cooled to −10° C. The precipitate is a very dense oil which is separated by decanting and dissolved in 15 ml of boiling ethyl acetate. Finally the resulting solution is stirred at room temperature until solidification of the product is completed to give a crystalline yellow solid in the form of aciculae having a melting point of 173° to 175° C. (recrystallized from ethanol). The yield is 50%.

EXAMPLE 36

4-(2-Chlorophenyl)-6-ethyl-2-methyl-5-methoxycarbonyl-1,4-dihydropyridine-3-carboxylic acid-2-[N-(1,2-benzisothiazolyl-3(2H)one-1,1-dioxide)]-ethylester A mixture of 15 g (0.03M) of 2-(2-chlorobenzylidene)-acetyl acetic acid-2-[N-(1,2-benzisothiazolyl-3(2H)one-1,1-dioxide)]-ethylester (obtained as described in Example 19) and 4.47 g (0.03M) of 3-amino-4-methyl crotonic acid methylester is heated at reflux and stirred in 70 ml of absolute ethanol for 24 hours. After that time the solvent is removed by distillation under reduced pressure and the resulting oily residue dissolved in 15 ml of boiling ethyl acetate. Finally the resulting solution is stirred at room temperature until solidification of the product is completed to give a white solid having a melting point of 195° to 196° C. (recrystallized from ethanol). The yield is 68%.

EXAMPLE 37

2,6-Dimethyl-5-methoxycarbonyl-4-(2-nitrophenyl)-1,4-dihydropyridine-3-carboxylic acid-3-[N-(1,2-benzisothiazolyl-3(2H)one-1,1-dioxide)]-propylester A) 2-(2-Nitrobenzylidene)-acetyl acetic acid-3-[N-(1,2-benzisothiazolyl-3(2H)one-1,1-dioxide))-propylester A mixture of 50 g (0.15M) of acetyl acetic acid-3-[N-(1,2-benzisothiazolyl-3(2H)one-1,1-dioxide)]-propylester, 23.22 g (0.15M) of 2-nitrobenzaldehyde, 0.8 ml of piperidine and 0.5 ml of glacial acetic acid in 100 ml of anhydrous isopropanol is stirred at 60° C. for 3 hours, then at room temperature for 20 hours and finally at 0° C. for 2 hours. Thereafter the resulting suspension is stirred at room temperature for 3 hours to give a yellowish solid having a melting point of 112° to 113° C. (recrystallized from ethanol). The yield is 75%.

B) 2,6-Dimethyl-5-methoxycarbonyl-4-(2-
nitrophenyl)-1,4-dihydropyridine-3-carboxylic acid-
3-[N-(1,2-benzisothiazolyl-3(2H)one-1,1-dioxide)]-
propylester A mixture of 15 g (0.03M) of 2-(2-nitrobenzylidene)-
acetyl acetic acid-3-[N-(1,2-benzisothiazolyl-3(2H)one-1,1-
dioxide)]-propylester and 3.77 g (0.03M) of 3-amino cro-
tonic acid methylester is heated at reflux and stirred in 35 ml
of anhydrous isopropanol for 10 hours. After that time the
reaction mixture is cooled to room temperature to give a
yellow solid having a melting point of 191° to 193° C.
(recrystallized from ethanol). The yield is 62%.

EXAMPLE 38

2,6-Dimethyl-5-(2-methoxyethoxycarbonyl)-4-(2-
nitrophenyl)-1,4-dihydropyridine-3-carboxylic acid-
3-[N-(1,2-benzisothiazolyl-3(2H)one-1,1-dioxide)]-
propylester A mixture of 15 g (0.03M) of 2-(2-nitrobenzylidene)-
acetyl acetic acid-3-[N-(1,2-benzisothiazolyl-3(2H)one-1,1-
dioxide)]-propylester (obtained as described in Example 37)
and 5.21 g (0.03M) of 3-amino crotonic acid-2-
methoxyethylester is heated at reflux and stirred in 35 ml of
absolute ethanol for 18 hours. After that time the reaction
mixture is cooled to room temperature to give a very dense
oil which is separated by decanting and dissolved in 10 ml
of boiling ethyl acetate. Finally the resulting solution is
stirred at room temperature until solidification of the product
is completed to give a yellow solid having a melting point
of 146° to 150° C. with decomposition (recrystallized from
ethanol and ethyl acetate). The yield is 22%.

EXAMPLE 39

2,6-Dimethyl-5-isopropoxycarbonyl-4-(2-
nitrophenyl)-1,4-dihydropyridine-3-carboxylic acid-
3-[N-(1,2-benzisothiazolyl-3(2H)one-1,1-dioxide)]-
propylester A mixture of 15 g (0.03M) of 2-(2-nitrobenzylidene)-
acetyl acetic acid-3-[N-(1,2-benzisothiazolyl-3(2H)one-1,1-
dioxide)]-propylester (obtained as described in Example 37)
and 4.69 g (0.03M) of 3-amino crotonic acid isopropylester
is heated at reflux and stirred in 70 ml of isopropanol for 12
hours. After that time the reaction mixture is cooled to room
temperature to give a yellow solid having a melting point of
177° to 179° C. (recrystallized from ethyl acetate). The yield
is 60%.

EXAMPLE 40

4-(2,3-Dichlorophenyl)-2,6-dimethyl-5-
ethoxycarbonyl-1,4-dihydropyridine-3-carboxylic
acid-3-[N-(1,2-benzisothiazolyl-3(2H)one-1,1-
dioxide)]-propylester A) 2-(2,3-Dichlorobenzylidene)-acetyl acetic acid-
3-[N-(1,2-benzisothiazolyl-3(2H)one-1,1-dioxide)]-
propylester A mixture of 100 g (0.31M) of ethyl acetate-3-[N-(1,2-
benzisothiazolyl-3(2H)one-1,1-dioxide)]-propylester, 53.8 g
(0.31M) of 2,3-dichlorobenzaldehyde, 1.76 ml of piperidine
and 1.1 ml of glacial acetic acid in 200 ml of isopropanol is
stirred at 60° C. for 2 hours, then at room temperature for 24
hours and finally at 0° C. for 2 hours. After that time the
resulting suspension is allowed to stand overnight at −10° C.
to give a yellow solid having a melting point of 116° to 118°
C. (recrystallized from ethanol). The yield is 89%.

B) 4-(2,3-Dichlorophenyl)-2,6-dimethyl-5-
ethoxycarbonyl-1,4-dihydropyridine-3-carboxylic
acid-3-[N-(1,2-benzisothiazolyl-3(2H)one-1,1-
dioxide)]-propylester A mixture of 15 g (0.03M) of 2-(2,3-dichlorobenzylidene)
-acetyl acetic acid-3-[N-(1,2-benzisothiazolyl-3(2H)one-1,
1-dioxide)]-propylester and 4.15 g (0.03M) of 3-amino
crotonic acid ethylester is heated at reflux and stirred in 35
ml of anhydrous ethanol for 24 hours. After that time the
reaction mixture is cooled to −10° C. to give a very dense oil
which is obtained by decanting and dissolved in 15 ml of
boiling ethyl acetate. Finally the resulting solution is stirred
at room temperature for 3 hours to give a yellow solid
having a melting point of 172° to 174° C. (recrystallized
from ethyl acetate). The yield is 41%.

EXAMPLE 41

2,6-Dimethyl-5-ethoxycarbonyl-4-(2-nitrophenyl)-1,
4-dihydropyridine-3-carboxylic acid-3-[N-(1,2-
benzisothiazolyl-3(2H)one-1,1-dioxide)]-propylester A mixture of 15 g (0.03M) of 2-(2-nitrobenzylidene)-
acetyl acetic acid-3-[N-(1,2-benzisothiazolyl-3-(2H)one-1,
1-dioxide)]-propylester (obtained as described in Example
37) and 4.23 g (0.03M) of 3-amino crotonic acid ethylester
is heated at reflux and stirred in 35 ml of anhydrous
isopropanol for 16 hours. After that time the reaction mix-
ture is cooled to room temperature to give a crystalline
yellow solid having a melting point of 166° to 168° C.
(recrystallized from ethanol). The yield is 60%.

EXAMPLE 42

4-(2,3-Dichlorophenyl)-2,6-dimethyl-5-
isopropoxycarbonyl-1,4-dihydropyridine-3-
carboxylic acid-3-[N-(1,2-benzisothiazolyl-3(2H)
one-1,1-dioxide)]-propylester A mixture of 15 g (0.03M) of 2-(2,3-dichlorobenzylidene)
acetyl acetic acid-3-[N-(1,2-benzisothiazolyl-3(2H)one-1,1-
dioxide)]-propylester (obtained as described in Example 40)
and 4.61 g (0.03M) of 3-amino crotonic acid isopropylester
is heated at reflux and stirred in 35 ml of anhydrous
isopropanol for 24 hours. After that time the reaction mix-
ture is cooled to −10° C. to give a very dense oil which is
separated by decanting and dissolved in 15 ml of boiling
ethyl acetate. Finally the resulting solution is stirred at room
temperature until solidification of the product is completed
to give a pale yellow solid in the form of crystalline particles
having a melting point of 165° to 167° C. (recrystallized
from ethanol). The yield is 70%.

EXAMPLE 43

2,6-Dimethyl-5-ethoxycarbonyl-4-(2-
trifluoromethylphenyl)-1,4-dihydropyridine-3-
carboxylic acid-3-[N-(1,2-benzisothiazolyl-3(2H)
one-1,1-dioxide)]-propylester A mixture of 15 g (0.03M) of 2-(2-
trifluoromethylbenzylidene)-acetyl acetic acid-3-[N-(1,2-
benzisothiazolyl-3(2H)one-1,1-dioxide)]-propylester
(obtained as described in Example 33) and 4.02 g (0.03M)
of 3-amino crotonic acid ethylester is heated at reflux and
stirred in 35 ml of absolute ethanol for 20 hours. After that time the reaction mixture is cooled to room temperature to give a yellow solid having a melting point of 153° to 155° C. (recrystallized from ethanol). The yield is 78%.

EXAMPLE 44

2,6-Dimethyl-4-(3-nitrophenyl)-5-[(2-tetrahydropyranyl)methoxycarbonyl]-1,4-dihydropyridine-3-carboxylic acid-2-[N-(1,2-benzisothiazolyl-3(2H)one-1,1-dioxide)]-ethylester A mixture of 30 g (0.07M) of 2-(3-nitrobenzylidene)-acetyl acetic acid-2-[N-(1,2-benzisothiazolyl-3(2H)one-1,1-dioxide)]-ethylester (obtained as described in Example 3) and 13.45 g (0.07M) of 3-amino crotonic acids.(2-tetrahydropyranyl)-methylester is heated at reflux And stirred in 70 ml of absolute ethanol for 8 hours. After that time the reaction mixture is maintained overnight at room temperature to give a yellow solid having a melting point of 189° to 191° C. (recrystallized from ethyl acetate). The yield is 79%.

EXAMPLE 45

2,6-Dimethyl-5-(2-methoxyethoxycarbonyl)-4-(2-trifluoromethylphenyl)-1,4-dihydropyridine-3-carboxylic acid-3-[N-(1,2-benzisothiazolyl-3(2H)one-1,1-dioxide)]-propylester A mixture of 15 g (0.03M) of 2-(2-trifluoromethylbenzylidene)-acetyl acetic acid-3-(N-(1,2-benzisothiazolyl-3(2H)one-1,1-dioxide)]-propylester (obtained as described in Example 33) and 4.96 g (0.03M) of 3-amino crotonic acid-2-methoxyethylester is heated at reflux and stirred in 35 ml of absolute ethanol for 20 hours. After that time the reaction mixture is cooled to −10° C., the supernatant liquid decanted and the residue dissolved in 10 ml of boiling ethyl acetate. Finally the resulting solution is cooled to 5° C. to give a yellow solid having a melting point of 124° to 126° C. (recrystallized in ethanol). The yield is 35%.

EXAMPLE 46

6-Ethyl-2-methyl-5-methoxycarbonyl-4-(2-trifluoromethylphenyl)-1,4-dihydropyridine-3-carboxylic acid-3-[N-(1,2-benzisothiazolyl-3(2H)one-1,1-dioxide)]-propylester A mixture of 15 g (0.03M) of 2-(2-trifluoromethylbenzylidene)-acetyl acetic acid-3-[N-(1,2-benzisothiazolyl-3(2H)one-1,1-dioxide)]-propylester (obtained as described in Example 33) and 4.02 g (0.03M) of 3-amino-4-methyl crotonic acid methylester is heated at reflux and stirred in 35 ml of absolute ethanol for 20 hours. After that time the solvent is removed by distillation under reduced pressure and the resulting residue dissolved in 10 ml of boiling ethyl acetate. Finally the resulting solution is cooled to 5° C. to give a yellow solid having a melting point of 144° to 147° C. (recrystallized from ethyl acetate). The yield is 35%.

EXAMPLE 47

6-Ethyl-2-methyl-5-methoxycarbonyl-4-(3-nitrophenyl)-1,4-dihydropyridine-3-carboxylic acid-N-(1,2-benzisothiazolyl-3(2H)one-1,1-dioxide)-methylester A) 2-(3-Nitrobenhzylidene)-acetyl acetic acid-N-(1,2-benzisothiazolyl-3(2H)one-1,1-dioxide)-methylester A mixture of 50 g (0.33M) of 3-nitrobenzaldehyde, 98.36 g (0.33M) of acetyl acetic acid-N-(1,2-benzisothiazolyl-3 (2H)one-1,1-dioxide)-methylester, 1.9 ml of piperidine and 1.16 ml of glacial acetic acid in 215 ml of anhydrous isopropanol is stirred at 60° C. for 4 hours, then at room temperature for 24 hours and finally at 0° C. for 3 hours. After that time the resulting suspension is cooled overnight to −10° C., then the supernatant liquid decanted and the resulting residue dissolved in 20 ml of boiling ethyl acetate. Finally the resulting solution is stirred at room temperature until solidification of the product is completed to give a pale yellow solid having a melting point of 175° to 177° C. which is used in the next step without further purification. The yield is 65%.

B) 6-Ethyl-2-methyl-5-methoxycarbonyl-4-(3-nitrophenyl)-1,4-dihydropyridine-3-carboxylic acid-N-(1,2-benzisothiazolyl-3(2H)one-1,1-dioxide)-methylester A mixture of 15 g (0.035M) of 2-(3-nitrobenzylidene)-acetyl acetic acid-N-(1,2-benzisothiazolyl-3(2H)one-1,1-dioxide)-methylester and 4.5 g (0.035M) of 3-amino-4-methyl crotonic acid methylester is heated at reflux and stirred in 35 ml of absolute ethanol for 12 hours. After that time the reaction mixture is cooled to 5° C. to give a yellow solid having a melting point of 176° to 178° C. (recrystallized from ethanol). The yield is 47%.

EXAMPLE 48

4-(2-Chlorophenyl)-2,6-dimethyl-5-(2-methoxyethoxycarbonyl)-1,4-dihydropyridine-3-carboxylic acid-3-[N-(1,2-benzisothiazolyl-3-(2H)one-1,1-dioxide)]-propylester A mixture of 15 g (0.03M) of 2-(2-chlorobenzylidene)-acetyl acetic acid-3-[N-(1,2-benzisothiazolyl-3(2H)one-1,1-dioxide)]-propylester (obtained as described .in Example 32) and 5.33 g (0.03M) of 3-amino crotonic acid-2-methoxyethylester is heated at reflux and stirred in 35 ml of absolute ethanol for 24 hours. After that time the solvent is removed by distillation under reduced pressure and the resulting residue dissolved in 15 ml of boiling diisopropylether. Finally the resulting solution is cooled overnight to −10° C. to give a yellow solid having a melting point of 99° to 101° C. (recrystallized from ethanol). The yield is 63%.

EXAMPLE 49

5-Tert.-butoxycarbonyl-4-(2-chlorophenyl)-2,6-dimethyl-1,4-dihydropyridine-3-carboxylic acid-2-[N-(1,2-benzisothiazolyl-3(2H)one-1,1-dioxide)]-ethylester A mixture of 13.47 g (0.03M) of 2-(2-chlorobenzylidene)-acetyl acetic acid-2-[N-(1,2-benzisothiazolyl-3(2H)one-1,1-dioxide)]-ethylester (obtained as described in Example 19) and 4.88 g (0.03M) of 3-amino crotonic acid-tert.-butylester is heated at reflux and stirred in 40 ml of absolute ethanol for 15 hours. After that time the reaction mixture is cooled to room temperature to give a white solid having a melting point of 173° to 175° C. (recrystallized from ethanol). The yield is 66%.

EXAMPLE 50

5-Tert.-butoxycarbonyl-4-(2,3-dichlorophenyl)-2,6-dimethyl-1,4-dihydropyridine-3-carboxylic acid-3-[N-(1,2-benzisothiazolyl-3(2H)one-1,1-dioxide)]-propylester A mixture of 15 g (0.03M) of 2-(2,3-dichlorobenzylidene)-acetyl acetic acid-3-[N-(1,2-benzisothiazolyl-3(2H)one-1, 1-dioxide)]-propylester (obtained as described in Example 40) and 5.06 g (0.03M) of 3-amino crotonic acid-tert.-butylester is heated at reflux and stirred in 40 ml of absolute ethanol for 20 hours. After that time the reaction. mixture is cooled to room temperature to give a yellow solid having a melting point of 201° to 203° C. (recrystallized from ethanol). The yield is 58%.

EXAMPLE 51

5-Tert.-butoxycarbonyl-2,6-dimethyl-4-(3-nitrophenyl)-1,4-dihydropyridine-3-carboxylic acid-2-[N-1,2-benzisothiazolyl-3(2H)one-1,1-dioxide)]-ethylester A mixture of 15 g (0.03M) of 2-(3-nitrobenzylidene)-acetyl acetic acid-2-N-(1,2-benzisothiazolyl-3(2H)one-1,1-dioxide)]-ethylester (obtained as described in Example 3) and 5.31 g (0.03M) of 3-amino crotonic acid-tert.-butylester is heated at reflux and stirred in 40 ml of absolute ethanol for 12 hours. After that time the solvent is removed by distillation under reduced pressure and the resulting residue dissolved in 10 ml of boiling methanol. Finally the resulting solution is stirred at room temperature until solidification of the product is completed to give a yellow solid in the form of prisms having a melting point of 153° to 155° C. (recrystallized from ethanol). The yield is 74%.

EXAMPLE 52

4-(2-Chlorophenyl)-2,6-dimethyl-5-isopropoxycarbonyl-1,4-dihydropyridine-3-carboxylic acid-3-[N-(1,2-benzisothiazolyl-3(2H)one-1,1-dioxide)]-propylester A mixture of 15 g (0.03M) of 2-(2-chlorobenzylidene)-acetyl acetic acid -3-[N-(1,2-benzisothiazoly-3(2H)one 1,1-dioxide)]-propylester (obtained as described in Example 32) and 4.8 g (0.03M) of 3-amino crotonic acid-isopropylester is heated at reflux and stirred in 35 ml of absolute ethanol for 24 hours. After that time 20 ml of solvent are removed by distillation under reduced pressure and the resulting solution is cooled overnight to −10° C. to give a yellow solid having a melting point of 142° to 145° C. (recrystallized from ethanol). The yield is 87%.

EXAMPLE 53

5-Tert.-butoxycarbonyl-2,6-dimethyl-4-(3-nitrophenyl)-1,4-dihydropyridine-3-carboxylic acid-N-(1,2-benzisothiazolyl-3(2H)one-1,1-dioxide)-methylester A mixture of 15 g (0.03M) of 2-(3-nitrobenzylidene)-acetyl acetic acid-N-1,2-benzisothiazolyl-3(2H)one-1,1-dioxide)-methylester (obtained as described in Example 47) and 5.48 g (0.03M) of 3-amino crotonic acid-tert.-butylester is heated at reflux and stirred in 80 ml of anhydrous ethanol for 12 hours. After that time the reaction mixture is cooled to room temperature to give a crystalline yellow solid in the form of prisms having a melting point of 207° to 209° C. (recrystallized from ethanol). The yield is 70%.

EXAMPLE 54

5-Tert.-butoxycarbonyl-2,6-dimethyl-4-(2-nitrophenyl)-1,4-dihydropyridine-3-carboxylic acid-2-[N-(1,2-benzisothiazolyl-3(2H)one-1,1-dioxide)]-ethylester A) 2-(2-Nitrobenzylidene)-acetyl acetic acid-2-[N-(1,2-benzisothiazolyl-3(2H)one-1,1dioxide)]-ethylester A mixture of 100 g (0.66M) of 2-nitrobenzaldehyde, 206 g (0.66M) of acetyl acetic acid-2-[N-(1,2-benzisothiazolyl-3(2H)one-1,1-dioxide)]-ethylester, 3 ml of piperidine and 8 ml of glacial acetic acid in 620 ml of anhydrous isopropanol is maintained at 40° C. for 0.5 hours with stirring, then at room temperature for 16 hours and finally at 0° C. for 1 hour. Thereafter the resulting solid is filtered off and washed with boiling methanol to give a pale yellow solid having a melting point of 161° to 163° C. The yield is 85%.

5-Tert.-butoxycarbonyl-2,6-dimethyl-4-(2-nitrophenyl)-1,4-dihydropyridine-3-carboxylic acid-2-[N-(1,2-benzisothiazolyl-3(2H)one-1,1-dioxide)]-ethylester A mixture of 15 g (0.03M) of 2-(2-nitrobenzylidene)-acetyl acetic acid-2-[N-(1,2-benzisothiazolyl-3(2H)one-1,1-dioxide)]-ethylester and 5.31 g (0.03M) of 3-amino crotonic acid-tert.-butylester is heated at reflux and stirred in 40 ml of absolute ethanol for 12 hours. After that time the reaction mixture is cooled overnight to −10° C., the supernatant liquid decanted and the resulting residue dissolved in 15 ml of boiling ethyl acetate. Finally the resulting solution is stirred at room temperature until solidification of the product is completed to give a yellow solid having a melting point of 164° to 165° C. (recrystallized from ethanol). The yield is 57%.

EXAMPLE 55

5-Tert.-butoxycarbonyl-4-(2,3-dichlorophenyl)-2,6-dimethyl-1,4-dihydropyridine-3-carboxylic acid-2-[N-(1,2-benzisothiazolyl-3(2H)one-1,1-dioxide)]-ethylester A mixture of 15 g (0.03M) of 2-(2,3-dichlorobenzylidene)-acetyl acetic acid-2[N-(1,2benzisothiazolyl-3(2H)one-1,1-dioxide)]-ethylester (obtained as described in Example 15) and 5.04 g. (0.03M) of 3-amino crotonic acid-tert.-butylester is heated at reflux and stirred in 40 ml of absolute ethanol for 14 hours. After that time the solvent is removed by distillation under reduced pressure and the resulting residue dissolved in 15 ml of boiling ethyl acetate. Finally the resulting solution is stirred at room temperature until solidification of the product is completed to give a yellow solid having a melting point of 160° to 163° C. (recrystallized from ethyl acetate). The yield is 80%.

Biological Tests

The vasodilatory effects are tested as follows: an isolated aorta of the thorax of white New Zealand rabbits is secured in an organ bath. The contractile activity of the helical throacic aorta strip is recorded after depolarization with Krebs solution without calcium (35 mM, potassium) and addition of external calcium pulses (1.5 mM). The compounds are added in increasing concentrations before calcium is reintroduced. The $IC_{50}$ values (negative logarithm of the molar concentration required to block by 50% the calcium-induced contraction of $K^+$-depolarized rabbit aorta) are calculated by interpolation of the corresponding curves.

The tissue selectivity is measured from the ratio between the $IC_{50}$ value, the molar concentration required to depress contraction in the left stimulated isolated rabbit atrium by 50%, and the $IC_{50}$ value which is obtained in the $K^+$-depolarized rabbit aorta.

The left rabbit atrium is isolated and secured in an organ bath at a tension of 1 g in Krebs solution gassed with 95% $O_2$ and 5% $CO_2$ at 30° to 32° C. The electrical stimulation is fixed at 1 Hz. After one hour equilibration the percentage contraction is set at 100%, increased concentrations of the compounds are added to the bath every 15 minutes and the changes in the contractile force are recorded. The $IC_{50}$ values are calculated by interpolation from the concentration-effect relationship determined in each of the experiments.

The antihypertensive activity of the compounds of the invention is tested in spontaneously hypertensive rats (SHR) of Okamoto strain. Systolic blood pressure is monitored by tail plethysmography. The animals are trained for two weeks for the monitoring process. On the day of the experiment the rats are placed in an oven for two hours at 31°±1° C. and blood pressure is recorded graphically. The measurement recorded is the average of five measurements taken in each case. Only animals with basic values of systolic blood pressure over 170 mm Hg are considered hypertensive. After 24 hours fasting the compound to be tested (20 mg/kg) and/or a carrier (20% PEG 400 in 0.5% aqueous methyl cellulose (10 ml/kg)) is orally administered to the selected hypertensive animals by means of a gastric cannula. The values are expressed in percentage variation 2 hours after treatment. The results are shown in table 2.

The duration of effect is recorded in the isolated rabbit aorta of the thorax. After contraction of the depolarized rabbit aorta strips caused by the readdition of calcium has been blocked by the compounds ($10^{-7}$M), the preparation is repeatedly washed every 30 minutes for up to 4 hours with subsequent calcium induced pulses. The percentage recovery of the initial contraction is recorded (table 3).

Nifedipine (2,6-dimethyl-4-(2-nitrophenyl)-1,4-dihydropyridine-3,5-dicarboxylic acid 3,5-dimethylester) is used as a comparative compound.

The vasoconstrictory effects are measured at low depolarizing conditions in rabbit aorta strips. 10 mM $K^+$ is used to obtain a low starting concentration. Subsequently, increasing concentrations of the test compound are added in order to achieve an increase in contraction.

The $EC_{50}$ (negative logarithm of the molar concentration required to increase the calcium induced contraction of low $K^+$ depolarized rabbit aorta by 50%) is analysed by interpolation of the corresponding concentration-response curves (table 4).

The vasoconstrictory properties of the compound 53 are compared with those of the known calcium channel activator 2,6-dimethyl-3-nitro-4-(2-trifluoromethylphenyl)-1,4-dihydropyridine-5-carboxylic acid methylester (BayK-8644).

TABLE I $IC_{50}$ values of compounds of different examples obtained in rabbit aorta strips predepolarized with high calcium doses and vascular selectivity indices calculated from the ratio of the corresponding $IC_{50}$ values obtained in left stimulated rabbit atrium and in rabbit aorta.

| Compound according to Example | $IC_{50}$ (nM) Aorta | Selectivity index (Atrium/Aorta) |
| --- | --- | --- |
| 25 | 1.02 | 205 |
| 3 | 0.27 | 137 |
| 16 | 0.25 | 2744 |
| 17 | 0.49 | 152 |
| 18 | 0.98 | 103 |
| 29 | 0.76 | 686 |
| 34 | 1.82 | 77 |
| 37 | 1.50 | 80 |
| 39 | 1.22 | 15 |
| 40 | 1.77 | 200 |
| 42 | 2.08 | 75 |
| 43 | 0.76 | 163 |
| 45 | 1.38 | 16 |
| 51 | 1.60 | 72 |
| 52 | 1.30 | 37 |
| 54 | 0.70 | 41 |
| 55 | 2.30 | 122 |
| nifedipine | 2.90 | 39 |

TABLE II

Percentage change in systolic blood pressure after single oral dose (20 mg/kg) of compounds to SHR.

| Compound according to Example | % Change |
| --- | --- |
| 25 | −1.01 |
| 3 | 19.74 |
| 16 | 7.45 |
| 17 | 27.27 |
| 18 | 37.09 |
| 29 | 35.05 |
| 34 | 11.07 |
| 37 | 6.83 |
| 39 | 3.61 |
| 40 | 35.51 |
| 42 | 10.54 |
| 43 | 18.65 |
| 45 | 10.96 |
| 51 | 24.63 |
| 52 | 19.38 |
| 54 | 23.42 |
| 55 | 35.84 |
| nifedipine | 35.43 |

TABLE III

Duration of the blocking effect of $10^{-7}$M of the compound on the contractions of the rabbit thoracic aorta strips.

| Compound according to Example | % Recovery of blocking after 4 hours |
| --- | --- |
| 25 | 1.61 |
| 3 | 0.00 |
| 16 | 0.00 |
| 17 | 14.46 |
| 18 | 0.52 |
| 29 | 0.00 |
| 34 | 6.05 |
| 37 | 18.82 |
| 39 | 0.24 |
| 40 | 0.00 |
| 42 | 0.00 |
| 43 | 1.23 |
| 45 | 18.33 |
| 51 | 0.00 |
| 52 | 0.51 |
| 54 | 0.23 |
| 55 | 0.00 |
| nifedipine | 71.59 |

TABLE IV

EC$_{50}$ values for a test compound obtained in rabbit aorta strips predepolarized with 10 mM K$^+$.

| Compound according to Example | EC$_{50}$ (nM) Aorta |
|---|---|
| 53 | 9.3 |
| BayK-8644 | 13.0 |

We claim:

1. A 1,4-dihydropyridine compound of the formula

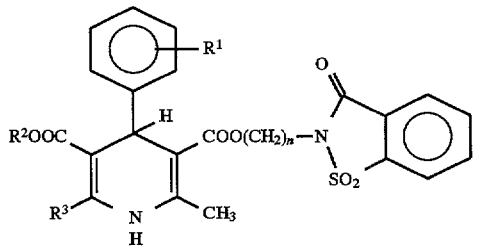

(I)

wherein

R$^1$ is nitro or trifluoromethyl, chlorine or two chlorines in 2 and 3 position, R$^2$ is branchless or branched saturated C$_1$–C$_8$-alkyl or a group of the formula—W—O—Z, whereby W is branchless C$_1$–C$_3$-alkylene and Z is branchless C$_{1-3}$-alkyl, R$^3$ is methyl or ethyl and n is an integer of the value of 1, 2 or 3.

2. A compound according to claim 1, selected from the group consisting of 2,6-dimethyl-5-ethoxycarbonyl-4-(2-trifluoromethylphenyl)-1,4-dihydropyridine-3-carboxylic acid-2-[N-(1,2-benzisothiazolyl-3(2H) one-1,1-dioxide)]-ethylester, 2,6-dimethyl-5-isopropoxycarbonyl-4-(2-trifluoromethyl-phenyl)-1,4-dihydropyridine-3-carboxylic acid-2-[N-(1,2-benzisothiazolyl-3(2H) one-1,1-dioxide)]-ethylester, 4-(2,3-dichlorophenyl)-2,6-dimethyl-5-methoxycarbonyl-1,4-dihydropyridine-3-carboxylic acid-3-[N-(1,2-benzisothiazolyl-3(2H) one-1,1-dioxide)]-propylester, 4-(2,3-dichlorophenyl)-2,6-dimethyl-5-ethoxycarbonyl-1,4-dihydropyridine-3-carboxylic acid-3-[N-(1,2-benzisothiazolyl-3(2H) one-1,1-dioxide)]-propylester, 5-tert.-butoxycarbonyl-2,6-dimethyl-4-(2-nitrophenyl)-1,4-dihydropyridine-3-carboxylic acid-2[N-(1,2-benzisothiazolyl-3(2H)one-1,1-dioxide)]-ethylester, and 5-tert.-butoxycarbonyl-4-(2,3-dichlorophenyl)-2,6-dimethyl-1,4-dihydropyropyridine-3-carboxylic acid-2-[N-(1,2-benzisothiazolyl-3(2H) one-1,1-dioxide)]-ethylester.

3. The compound 2,6-dimethyl-4-(3-nitrophenyl)-5-[(2-tetrahydropyranyl)-methoxycarbonyl]-1,4-dihydropyridine-3-carboxylic acid-2-[N-(1,2-benzisothiazolyl-3(2H)one-1,1-dioxide)]-ethylester.

4. A pharmaceutical composition which comprises at least one compound according to claims 1 or 2 and a physiologically acceptable carrier.

5. A pharmaceutical composition according to claim 4 for the treatment of hypertension and vasoconstriction.

6. A pharmaceutical composition which comprises the compound of claim 3 and a physiologically acceptable carrier.

7. A pharmaceutical composition for the treatment of hypotension which comprises the compound of claim 3 and a physiologically acceptable carrier.

* * * * *